United States Patent [19]

Van de Velde

[11] Patent Number: 5,923,399
[45] Date of Patent: Jul. 13, 1999

[54] SCANNING LASER OPHTHALMOSCOPE OPTIMIZED FOR RETINAL MICROPHOTOCOAGULATION

[75] Inventor: Frans J. Van de Velde, Boston, Mass.

[73] Assignee: Jozef F. Van de Velde, Oosterzele, Belgium

[21] Appl. No.: 08/755,448

[22] Filed: Nov. 22, 1996

[51] Int. Cl.$^6$ ..................................................... A61B 3/10
[52] U.S. Cl. ........................................... 351/221; 351/206
[58] Field of Search ................................... 351/200, 205, 351/206, 210, 211, 221

[56] References Cited

U.S. PATENT DOCUMENTS

| | | | |
|---|---|---|---|
| 4,213,678 | 7/1980 | Pomerantzeff et al. | 351/210 |
| 4,477,159 | 10/1984 | Mizuno et al. | 351/221 |
| 4,669,837 | 6/1987 | Schirmer et al. | 351/221 |
| 4,764,005 | 8/1988 | Webb et al. | 351/205 |
| 5,152,295 | 10/1992 | Kobayashi et al. | 351/206 |
| 5,308,919 | 5/1994 | Minnich | 351/221 |
| 5,568,208 | 10/1996 | Van de Velde | 351/221 |

OTHER PUBLICATIONS

Nasemann and Burk, eds., Scanning laser ophthalmoscopy . . . ISBN 3–92 0836–01–7, Chapters 1 and 2, pp. 23–46.

Pflibsen et al., Fundus reflectometry for photocoagulation dosimetry in Applied Optics, vol. 28, No. 6, 1989, pp. 1084–1095.

Pomerantzeff et al., A method to predetermine the correct photo . . . in Archives of ophthalmology, vol. 101, No. 6, 1983, pp. 949–953.

*Primary Examiner*—Huy Mai

[57] ABSTRACT

A combination of scanning laser ophthalmoscope and therapeutic laser source expands the range of clinical applications of the conventional scanning laser ophthalmoscope, being capable of simultaneous imaging, microperimetry and the delivery of therapeutic laser applications to the retina in a preferred non-contact mode. The combination, including a therapeutic laser source, optic-mechanical Maxwellian view coupling device allowing a similar Maxwellian view entrance location in the eye for both the scanning laser ophthalmoscope and therapeutic laser source, and real-time electronic registration of the therapeutic beam location, permits precise positioning and dosage of the retinal applications. Additional safety mechanisms include a shutter activation based on digital image processing techniques.

3 Claims, 4 Drawing Sheets

SCANNING LASER OPHTHALMOSCOPE OPTIMIZED FOR RETINAL MICROPHOTOCOAGULATION

BACKGROUND-CROSS REFERENCE TO RELATED APPLICATIONS

The invention uses the "Modified scanning laser ophthalmoscope for psychophysical applications" of U.S. Pat. No. 5,568,208, issued Oct. 22, 1996, and is related to U.S. Pat. No. 5,543,866, issued Aug. 6, 1996, entitled "Scanning laser ophthalmoscope for binocular imaging and functional testing".

BACKGROUND-FIELD OF INVENTION

This invention relates generally to instruments for examining the eye and specifically to an electro-optical ophthalmoscope for analyzing retinal function and performing retinal microphotocoagulation.

BACKGROUND-DESCRIPTION OF PRIOR ART

The ophthalmoscope is well known as an important aid for studying and examining the eye, and in particular, the fundus or retina of the eye. As a result of great interest in preserving man's eyesight, ophthalmoscopes of various constructions have been built and used. The latest version of the ophthalmoscope, a scanning laser ophthalmoscope (SLO), is particularly appealing because of its unique capability of combining the visualization of the retina or eye fundus with certain psychophysical testing procedures such as the study of preferred retinal loci of fixation (PRLs), potential acuity measurements, and microperimetry. With the scanning laser ophthalmoscope, a unique, precise correlation between retinal anatomy and function can be established. Different stimuli, used in visual psychophysics, can be projected onto the fundus with the help of the scanning laser ophthalmoscope. Overlay graphics are then used to display some stimulus characteristics such as size, location, and intensity on the fundus image in real-time. Detailed functional mapping of the fundus is thereby possible. Such retinal function mapping is now known to be very helpful to the retinal surgeon when planning therapeutic laser to the retina. These laser applications have been until now delivered to the retina with a different instrument. This implies that simultaneous psychophysical testing or even the injection of diagnostic angiographic dyes such as fluorescein or indocyanin green during the laser treatment is impossible.

U.S. Pat. No. 4,213,678, issued Sep. 29, 1980, discloses a scanning laser ophthalmoscope for the purpose of simultaneously diagnosing and treating retinal disease using two different intensity levels of the scanning laser beam. One intensity range can be used for monochromatic imaging, angiographies or psychophysical testing while a much higher level of the same laser beam or a different colinear scanning laser beam is useful for thermal retinal coagulation. This novel approach however is not ideal because of the technical difficulties in implementing safety controls for such scanning therapeutic laser beam, the difficulty in modulating the scanning laser beam over a range from non-coagulating to coagulating powers at video rate, and the non-thermal complications of a very high intensity pulsed laser beam at video rate.

It is nevertheless possible and evident for s/he skilled in the art, to combine optically an optical ophthalmoscope with a traditional non-scanning continuous laser source for the purpose of retinal photocoagulation. This combination, as described on multiple occasions in the prior art, is exemplified by the combination of a traditional slitlamp or indirect binocular ophthalmoscope with a therapeutic laser source. These combinations are typically provided with an aiming laser beam that is colinear with the therapeutic laser beam, a focussing device, a micro-manipulator for positioning the therapeutic laser beam onto the desired retinal location, and a combination of safety shutters and filters that interrupts the photocoagulating laser in case of malfunctioning of the instrument. However, until the present invention, all coagulating ophthalmoscopes have been limited when consistent minimal intensity laser applications on the retina are desired. The thermal changes caused by such laser applications are very difficult if not impossible to visualize and therefore the desired end point of the application is often exceeded. This is even accentuated by the fact that the surgeon, upon recognizing the minimal changes on the retina, will need a minimal reaction time delay to stop the therapeutic laser, and during this interval the laser continues to deliver heat to the retina. Also, it is difficult to avoid re-application of laser to the same area or too close to another laser application because of the low visibility of the effects of a minimal application during the current treatment session or at a later session.

Furthermore, eye movements and changes in the subject's fixation have hitherto limited the accuracy and ease of performing either high resolution microperimetry or applying microscopic laser to the fundus. Since the reaction time of the surgeon may exceed 200 ms, a 100 ms application can then be wrongly targeted on the retina in the case of fixation loss.

Further automation will require a precise mapping of the positioning of the micro-manipulator to the fundus coordinates. This coupling is very difficult to realize mechanically, difficult to calibrate and prone to error. At present there is no constant mapping or linkage between the position of the micromanipulator and the position of the aiming beam or therapeutic beam on the retina in any known combination of ophthalmoscope and therapeutic laser source.

OBJECTS AND ADVANTAGES

The principal object of this invention is therefore to provide a single instrument, a scanning laser ophthalmoscope, with the capability of simultaneous microperimetric testing, angiographic testing, and preferably non-contact microphotocoagulation with the necessary controls for the dosage and optimal placement of microscopic laser applications.

Digital image processing techniques are used to obtain optimal placement of the laser applications. In general, this is accomplished by registering the localization of the aiming beam or therapeutic beam in the video raster. Feature detecting algorithms are used for this purpose on the optically filtered visible light video images in real-time during the laser application. The therapeutic laser beam can be interrupted if e.g. the current localization of the application no longer matches with a preselected localization on the monochromatic real-time video image of the retina, as determined by digital image processing techniques such as normalized gray scale correlation. With other words, it is now possible with the instrument to deliver very mild consistent retinal laser applications, mostly involving the photoreceptor—RPE complex at predetermined locations and to store these positions as overlay graphics on a reference image of the fundus. This precise mapping can then be re-used for outlining further applications without the risk of retreating unrecognizable previous locations or putting the applications to close to each other. The mapping can also be used in the long term microperimetric evaluation of the impact of laser applications.

Further objects and advantages of the invention will become apparent from a consideration of the drawings and ensuing description.

REFERENCE NUMERALS IN DRAWINGS

Figure 1:
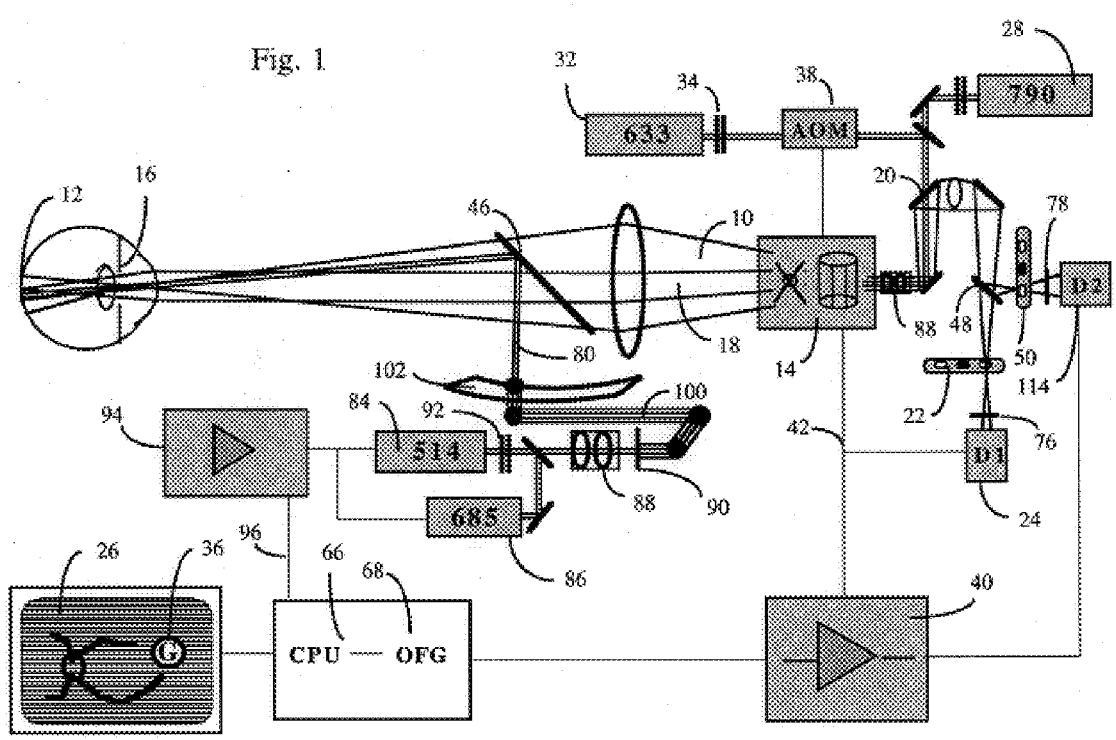
FIG. 1 is a schematic representation, illustrating the components of the scanning laser ophthalmoscope, optimized for microphotocoagulation. Two main parts can be distinguished. (1) A scanning laser ophthalmoscope, with two lasers, two detectors, and AOM. (2) A therapeutic laser with optical linkage to the scanning laser ophthalmoscope.

10 Scanning Gaussian beam of laser light (envelope)
12 Posterior pole of the eye
14 Scanners, including polygon and galvanometer
16 Pivot point of the Maxwellian view
18 Reflected and back scattered light from the eye
20 Beam separator
22 Pinhole at the retinal conjugate plane
24 Avalanche photodiode, D1
26 Video display monitor
28 Diode infra-red 780 nm laser
32 He—Ne red 632 nm laser
34 Pair of adjustable linear polarizers
36 Aiming beam location on the retina, visible as overlay
38 Acousto-optic modulator
40 Electronic circuitry of scanning laser ophthalmoscope
42 Distribution of common synchronization to different components
46 Beamsplitter
48 Beamsplitter
50 Confocal aperture
66 CPU with overlay frame grabber board
68 Additional overlay frame grabber board
76 Optical filter
78 Optical filter
80 Therapeutic laser beam (combined)
84 Therapeutic laser
86 Aiming beam, diagnostic laser
88 Collimator-telescope
90 Variable aperture
92 Safety filter(s)
94 Electronic interface therapeutic laser
96 I/O link
100 Adjustable mirror hinges
102 Positioning device
104 Framework
106 Support arc
108 Projecting means
110 Pivot point of therapeutic laser beam
112 Micromanipulator
114 Second avalanche photodetector with filters, D2
200 Fixation cross
210 Optically filtered visible light video image
220 Infra red retinal video image
240 gray scale pattern in search window
250 displacement of aiming beam
260 displacement of gray scale pattern in search window

DESCRIPTION AND OPERATION OF AN EMBODIMENT

A typical embodiment and method of operation of the scanning laser ophthalmoscope optimized for microphotocoagulation is illustrated in FIG. 1 through FIG. 6. The principles of scanning laser ophthalmoscopy are described in detail in the prior art. Features of the scanning laser ophthalmoscope relevant to the invention are further discussed.

I. THE SCANNING LASER OPHTHALMOSCOPE

A prefocused Gaussian beam of laser light 10, 0.5 mm in radius, is further focussed by the eye optic s to about $12\mu$ in radius at the retinal plane, and is scanned over the posterior pole of the eye 12 in a sawtooth manner with the help of scanning mirrors 14, currently a polygon and galvanometer. Both fast horizontal 15 KHz and slower vertical 60 Hz deflections of the flying laser spot are at standard video RS-170 rates and create the rectangular laser bean raster that is seen by the subject. A Maxwellian view is used in the illuminating means of the scanning laser ophthalmoscope: the pivot point 16 of the scanning laser beam varies minimally during scanning and is optimally situated in the iris plane with an average waist of less than 1 mm. Typically a rectangular area of 0.5 cm$^2$ on the retina is illuminated. This corresponds to a field of view of 40 degrees in diagonal or 32.7 degrees horizontally by 23.4 degrees vertically. The field of view can be changed from 40 to 20 degrees by switching optical components. In the 20 degree field of view, the pivot point 16 of the Maxwellian view is less variable in position during scanning, but wider in diameter at the entrance point of the Maxwellian view. In confocal viewing, the focusing i.e. positioning of the waist of the Gaussian beam then becomes critical to the point that it is possible to measure refraction for psychophysical purposes. Astigmatic errors cannot yet be compensated with the optics of the instrument itself. This would be easy to accomplish by incorporating a rotation dial of cross-cylinders. Also in the 20 degree field of view, it is more difficult to work around focal scattering or absorbing elements in the ocular media.

It is important to understand that the observer will not see a flying spot but rather a rectangle filled with thin horizontal stripes because of the temporal summation characteristics of the visual system. The reflected and back scattered light from the eye 18, now filling the pupil, is descanned over the same mirrors, separated from the illuminating beam at beam separator 20 and passed through a pinhole 22 at the retinal conjugate plane before reaching a fast and sensitive avalanche photodiode 24. This confocal detection is essential for obtaining high contrast pictures of the retina with infrared illumination. It is accomplished by eliminating stray light at the pinhole. The amount of light on the photodetector is translated into a voltage that modulates the intensity of an electron beam on the visual display cathode ray tube monitor 26. The electron beam moves synchronically with the scanning laser beam and a real-time video image of the fundus is likewise created on the display monitor. Typically two laser sources are aligned to illuminate the retina. The two lasers serve a different purpose. A high intensity diode infra-red 780 nm laser 28, electrically modulated and vertically polarized, is nearly invisible to the subject. It produces the retinal image on the display monitor. A colinear low intensity He—Ne red 632.8 nm red laser 32, modulated with a pair of adjustable linear polarizers 34 and horizontally polarized, is visible to the subject. It is used to draw e.g. a fixation cross 200 in the laser raster for projection onto the retina. These stimuli are created by amplitude modulation of the laserbeam at video rates as the red light passes through an acousto-optic modulator 3B. The acousto-optic modulator is driven by a standard video source, usually a computer overlay frame grabber card that contains the graphics information. This graphics generator is genlocked to the crystal clock of the electronic circuitry 40. Master timing signals are derived from the spinning polygon. It is important to understand the reason for using at least two different lasers. The scanning laser ophthalmoscope is very light efficient: about three orders of magnitude less light is necessary to visualize the fundus when compared with conventional ophthalmoscopes. However this light is still orders of magnitude the amount used for typical psychophysical testing. The problem is solved by using a 780 nm laser with sufficiently high output and for which the silicon detector of the scanning laser ophthalmoscope, but not the eye, is most sensitive, in combination with a low intensity 632 nm laser, for which the human eye is sensitive but usually insufficient for visualizing the fundus. This explains also why the stimuli which are perceived by the subject are usually not visible in the retinal picture, unless very bright. The exact position and characteristics of the stimuli can however be shown in real-time on the retinal image with the help of computer overlays as all image video out of the scanning laser ophthalmoscope, scanners, and graphics video into the acousto-optic modulator are synchronized to the same crystal clock 42.

The use of multiple detectors and multiple laser sources has been described in the prior art. Appropriate barrier filters are installed accordingly.

Surface-emitting quantum-well laser diodes, combined with a confocal two-dimensional array detector system mentioned in U.S. Pat. No. 4,213,678, are of increasing interest. This approach will offer the advantages of high packing densities on a wafer scale. An array of up to a million tiny individually modulated cylindrical $In_{0.2}Ga_{0.8}As$ surface-emitting quantum-well laser diodes with lasing wavelengths in the vicinity of 970 nm and shorter can substitute the traditional laser sources and scanners 14 of a scanning laser ophthalmoscope. This will render the device more compact, less noisy, and less susceptible to mechanical wear and tear.

II. THE OPTO-MECHANICAL LINKAGE BETWEEN SLO AND EXTERNAL LASER(S)

This chapter will describe the optical linkage between therapeutic laser and scanning laser ophthalmoscope, optimized for a non-contact method. Also, the important mechanism will be described by which the scanning laser ophthalmoscope and CPU are made aware of the cartesian position of the therapeutic or aiming laser beam on the retina, i.e. electronic registration of the retinal application location.

The disadvantages of using a scanning therapeutic laser beam that would be switched from a low energy to high energy status at the appropriate retinal location (Pommerantzeff, 1980) have been discussed before. Therefore, the therapeutic beam 80 should be maintained stationary, and allowed to move between laser applications only, using special transmission optics. The therapeutic laser 84 itself is well known in the art, either argon or currently diode laser, having the possibility of emitting different wavelengths, for example 514 nm. Often a second colinear low power aiming beam, for example a diode 685 nm 86 is provided. Alternatively, the therapeutic beam can serve as an aiming beam at much lower intensity. Also included in the optical pathway are a collimator-telescope 88 and variable aperture 90 for precisely adjusting the shape and size of the therapeutic laser beam. An important element of the photocoagulator is one or more safety shutters 92 or filters. A radiometer is build in to monitor power output. An electronic interface 94 connects the aforementioned elements with a control panel that is supervised by the surgeon. In addition, the combination of a scanning laser ophthalmoscope and therapeutic laser has an important I/O link 96, often a combination of TTL circuits, between the control circuits of the therapeutic laser and the host bus of the CPU. This electronic connection can make the CPU aware of when exactly the therapeutic laser is activated and also provides a means for activating the safety shutter under CPU control. The optical connection between the exit aperture of the laser and a positioning device is preferably made by a combination of extendable mirror hinges 100, instead of flexible fiber optics. A specially constructed positioning device 102 consists of a framework 104 that permits a support arc 106 to slide across. On the support arc is mounted a projecting means 108. This means can also slide along the arc and reflects the therapeutic laser light coming from the other mirrors in the transmission optics towards the eye. The two sliding movements allow the linkage device to project the therapeutic laser beam 80 perpendicular to a curved surface, e.g. a part of a sphere, such that the therapeutic laser beam 80 will have a pivot point 110 very similar to the pivot point 16 of the Maxwellian view of the scanning laser ophthalmoscope. The projecting means 108 itself is moved with the help of a micromanipulator 112 that is handled by the surgeon. Typically the positioning device is about 100 mm by 100 mm and will fit into an existing scanning laser ophthalmoscope to which it is fixed with support mounts. The beam is prefocused by a collimator-telescope 88 and further focused by the eye optics to a spot that can be as small as $10\mu$ radius on the retina. This spot then corresponds to the waist of a Gaussian beam.

A highly reflective beamsplitter 46 for the therapeutic wavelength but transparent for the other wavelengths of the scanning laser ophthalmoscope such as 632.8 nm and higher, is specifically coated for this purpose. This beamsplitter 46 renders the therapeutic laser beam 80 and scanning laser beams of the SLO coaxial towards the retina. Some of the therapeutic laser light 80 is however permitted to pass the beamsplitter 46, 48 in order to reach a photodetector 114 after returning from the retina. The light passing through the beamsplitter and not going towards the retina is carefully absorbed to avoid confusion with the therapeutic laser light 80 that is returning from the retina. All detectors 24, 114 are genlocked to a common time base for producing video output. This is useful in localizing the therapeutic laser spot onto the retina. For this purpose the detector 114 is provided with a barrier filter 78 to eliminate all light except the therapeutic laser wavelength returning from the retina. It is well known in the art of digital signal and image processing to retrieve the position of the isolated spot of light in the video image 210. Because of the common time base of infra-red SLO video images 220 and the detector 114 used for localizing the therapeutic laser beam 80, a precise indication of the position of the therapeutic beam is possible using overlay graphics 36. This information can then be stored, retrieved and further image processed. Several applications will then depend on the principle or mechanism outlined above. E.g. it is possible to plan laser applications in particular locations, it is further possible to store the treated locations for future reference and since the determination of the location of the therapeutic laser beam is happening in real-time, image registration as outlined below can determine whether the intended laser application location is still selected within a radius of acceptance. If misalignment occurs, the TTL circuit 96 can rapidly interrupt the therapeutic laser beam 80. This is advantageous since such interruption is likely to occur faster than human reaction would allow.

III. DIGITAL IMAGE PROCESSING

Figure 2:
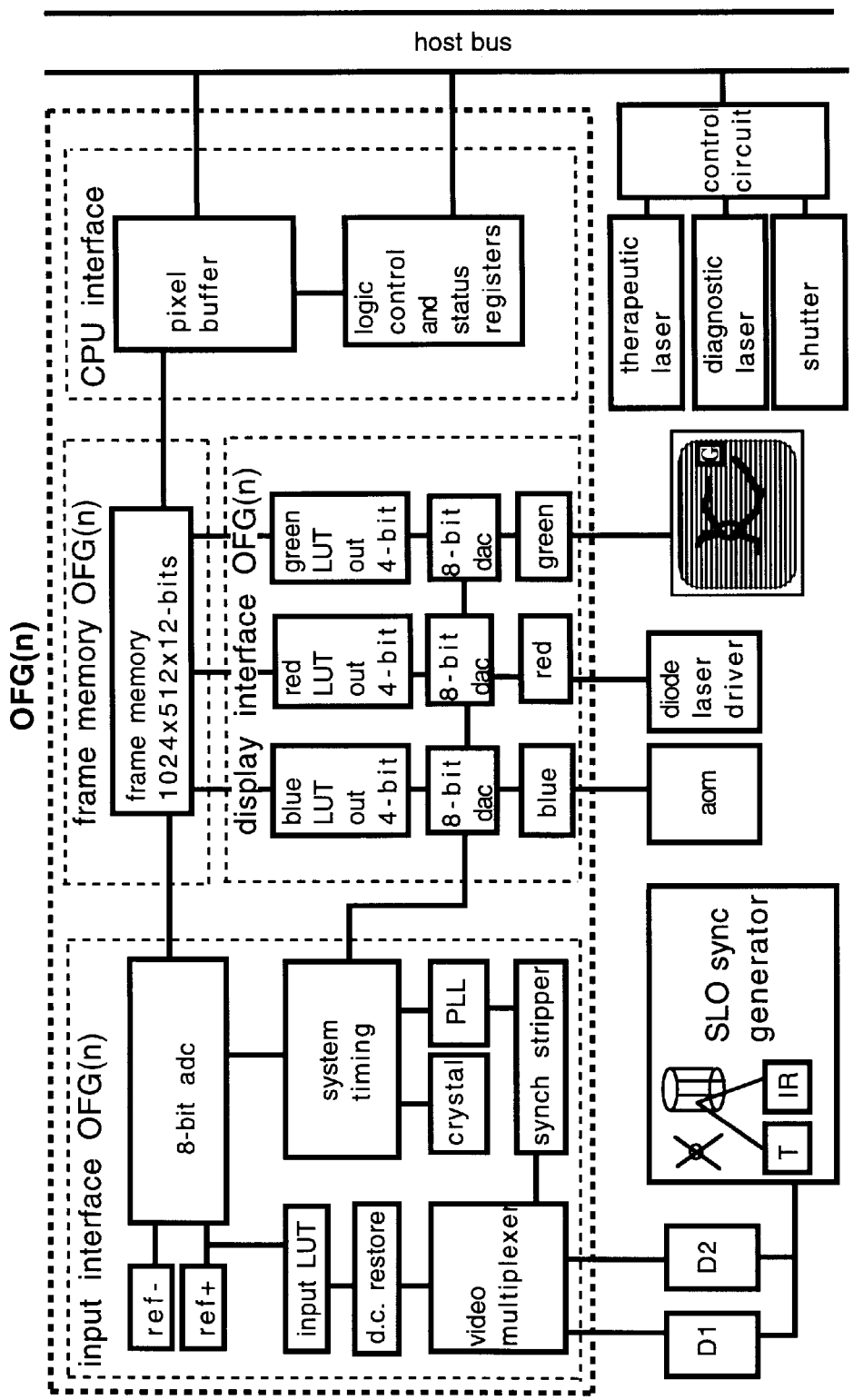
FIG. 2 illustrates the relation between the different electronical components of the scanning laser ophthalmoscope optimized for retinal microphotocoagulation. The overlay frame grabber card has an input interface, frame memory, display interface and CPU interface. Besides the OFG card(s), the host bus interacts with the control circuit of the therapeutic laser. The SLO electronics interface shows the synch generator, detectors, AOM circuitry and direct electrical modulation of diode laser. The following circuits are represented: (1) video-in pathway. (2) Video-out pathway. (3) the synchronization pathway and genlocking of other components of the system including adc, dac, detectors. (4) The TTL circuit to and from the therapeutic laser controlling the shutter and communicating activation of the therapeutic beam.
Figure 3:
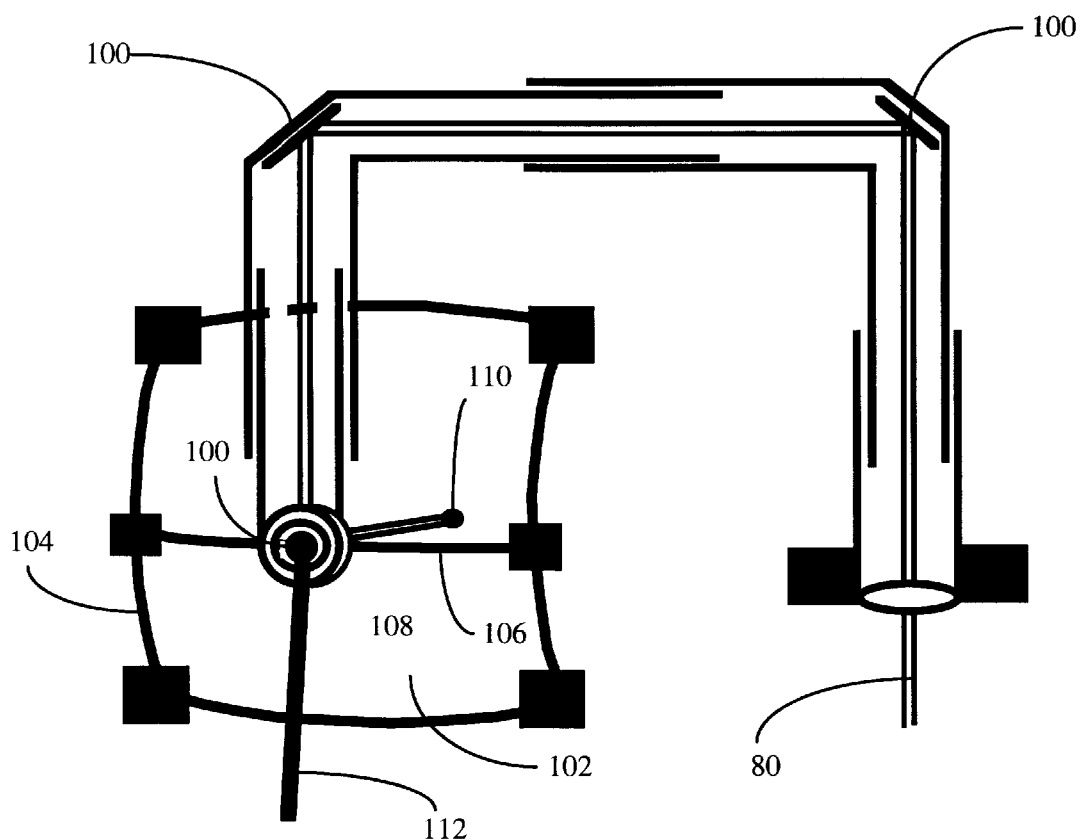
FIG. 3 details the opto-mechanical link between therapeutic laser and scanning laser ophthalmoscope.
Figure 4:
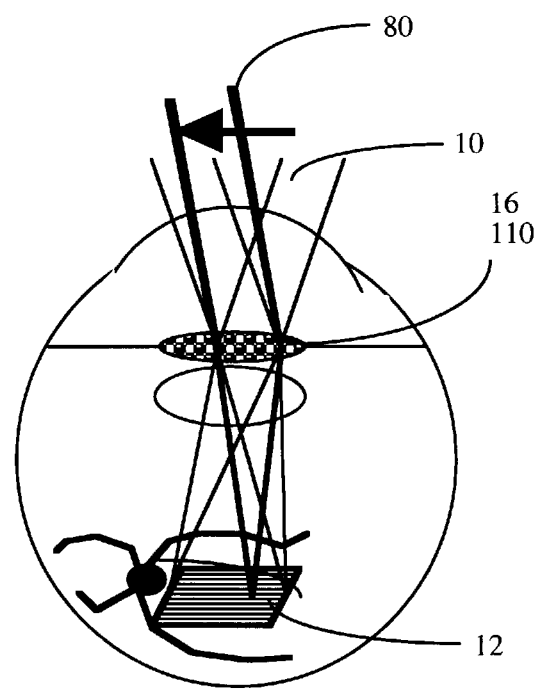
FIG. 4 illustrates the optical ray tracing of either diagnostic or therapeutic beam. Parallel rays in general illuminate the same retinal location but from a different angle. Non-parallel rays will sweep across the fundus. The Gaussian beam measures about 0.5 mm radius at the pupillary plane and tapers to about 12 micron radius on the retina plane. Ray tracing has been simplified. Thereby the point of entry in the pupillary plane can be a variable in the therapeutic application of laser, where the retinal location is kept unchanged. Movement of the scanning laser ophthalmoscope in a frontal plane will cause the rays of the incident laser beams to use a different part of the entrance pupil. This does not cause a significant shift in the position of the focus on the retinal image because the movement will displace the scanning laser beam rays in a parallel fashion, and parallel rays are focussed on the same retinal location. This retinal location will however be illuminated in an oblique fashion. Angulating the entrance laser beams will result in focussing on different retinal locations.
Figure 5:
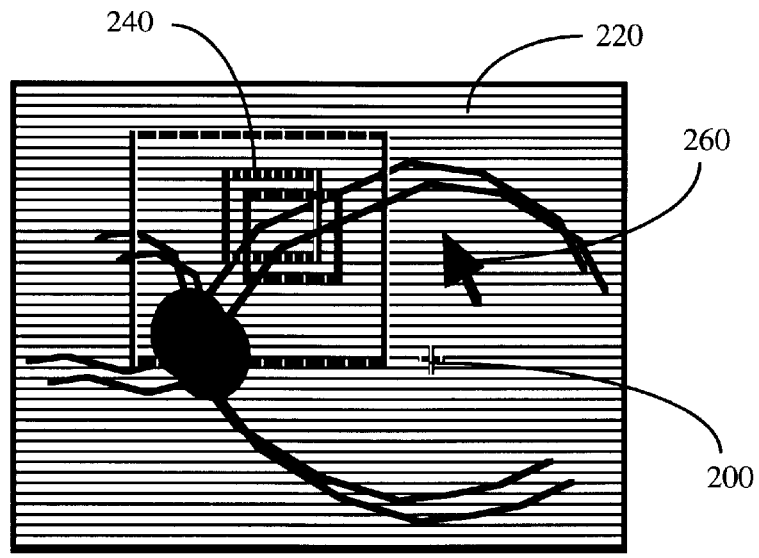
FIG. 5 illustrates the effect of a shift in fixation on the infra red retinal video image. Fixation cross position remains unchanged. This is in accordance with the movement of the small search window within the larger reference window. The search window contains a gray scale feature that can be used in normalized gray-scale correlation.
Figure 6:
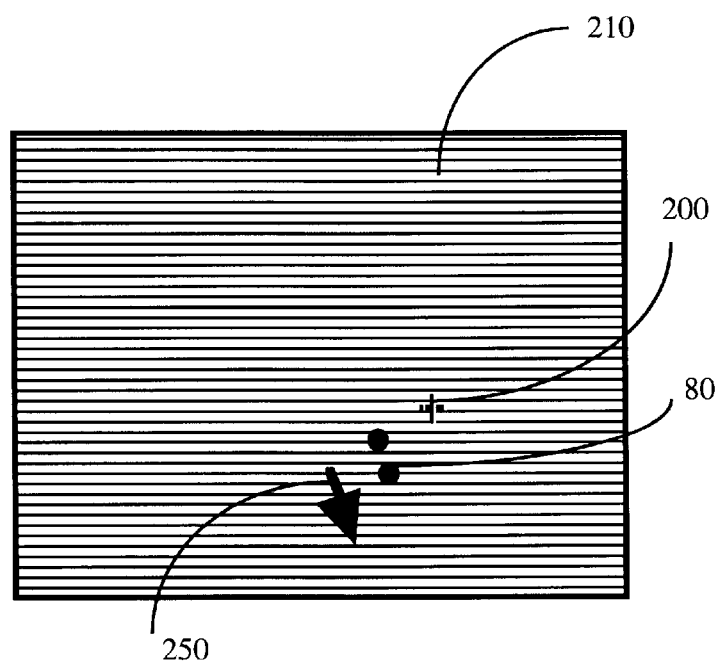
FIG. 6 illustrates the effect of a shift in aiming beam location on the optically filtered visible light image. Point P shifts to P'. These coordinates can be retrieved with image processing techniques.

Indispensable for handling the video that is output by the scanning laser ophthalmoscope and for the generation of graphics that will be projected onto the retina is the overlay frame grabber card, FIG. 2, For example the Imaging Technology OFG card in a 90 Mhz Pentium PC. This card can select between four video input sources, and digitizes the incoming video signal to eight bits of accuracy, at a rate of 60 fields per second (RS-170). On board frame memory can store two 512 by 480 pixel video frames. This versatility is important e.g. for the multiplexing of the signals from a multidetector SLO. The analog-to-digital converter on the frame grabber has programmable negative and positive reference values for calibrating the white and black video signal levels. A look-up table (LUT) controls the input video and can be used for preprocessing contrast and intensity. This feature is particularly useful in facilitating normalized gray scale correlation. In two-dimensional normalized gray-scale correlation a search pattern 240 is retrieved within the larger fixed reference pattern. Multiple search patterns can coexist. A second OFG board 68 within the same CPU 66 can perform this task using software provided by Imaging Technology, Inc, Bedford, Mass. A 7 degree rotational tolerance and 60 ms search time are acceptable. An additional four bits per pixel controls the switching between different output LUTs for individual pixels. Three independent output channels are provided. The output channels generate RS-170 video for pseudo-color display. Fast switching between output LUTs is an elegant solution for programming non-destructive graphic overlays. Non-destructive graphic overlays drawn into the incoming video signal are crucial for generating the stimuli in the laser raster of the SLO and symbols on the display monitor. Typically, the green output video will deliver the infra-red retinal image to the monitor 26 together with a symbolic graphics overlay 36 of the therapeutic beam location. The blue output of the original video signal is transformed into a graphics pattern. It is used to control the acousto-optic modulator 38 and defines the background and fixation cross 200 that is visible to the observer. The remaining red output can be used for different purposes. One option is a simultaneous control of the electric amplitude modulation of a diode laser. Another critical feature of the frame grabber is the possibility to synchronize to an external video source using the phase-locked loop. This is important since the timing signals provided by the high speed rotating polygon are slightly irregular.

At present, an acousto-optic modulator 38 is used to generate the video graphics in the laser beam raster of the scanning laser ophthalmoscope. A time delay exists between the update of the graphics overlay on the monitor and the actual change in intensity visible to the subject in the modulated laser raster. Calibration is of great importance (and has even medico-legal consequences) in assuring the correspondence between what is seen on the monitor and what is seen by the observer. The AOM delay can be calibrated by adjusting the position of the real image on the monitor of a bright enough stimulus to match its overlay. This is accomplished by programming the drawing of graphics to the SLO and to the monitor with an appropriate pixel interval (about 50 pixels or 3.5 $\mu s$).

Another very important function of the AOM is to provide the blanking of the video signal during the retrace intervals. This will prevent the visible scanning laser beam from being visible during vertical retrace.

SUMMARY, RAMIFICATIONS, AND SCOPE

The two main features of the scanning laser ophthalmoscope optimized for microphotocoagulation are a special Maxwellian view coupling device allowing control over the Maxwellian view entry location, and computer awareness of the location of aiming beam or therapeutic beam through usage of a common time base between different detectors.

With the device it is possible to visualize the retina and simultaneously perform microperimetry for the purposes documented in the related U.S. patents. Without changing instruments, the capability now exists to administer laser applications to the retina. Not having to change instruments, with different optical characteristics, is an important issue because of the instantaneous feedback with regard to the angiographic pattern and psychophysical response that one can obtain even during the treatment session. This feedback is represented on the same image that is used to direct the laser applications and will therefore enhance the precision of the treatment.

The specific optical linkage mechanism between the scanning laser ophthalmoscope and the therapeutic laser allows the use of essentially the same Maxwellian view for both the therapeutic laser and the scanning laser ophthalmoscope.

The ability to concentrate the thermal destruction to the photoreceptor-pigment epithelium complex may be very useful since selective removal of metabolically very active photoreceptor elements will reduce the consumption and competition for oxygen, glucose and other necessary elements, of which the transportation across the diseased retina is already impaired in early stages of age related maculopathy (e.g. thickening of Bruch's membrane, soft drusen permeability). The improved oxygenation, provided the choriocapillary layer is largely kept intact, in turn can reduce the production of angiogenetic "stress" stimuli produced by the RPE complex and in this way avoid the neovascularisation stage of age related macular disease. This mechanism may also lead to the disappearance of the drusen by reducing the workload of, and enhancing the productivity of the photoreceptor phagocytosis and renewal cycle. Microperimetry is useful to select the areas for laser treatment and then to follow-up on the functional status of the retina between the non-confluent applications. Possibly, retinal areas with diminished retinal function are more likely to attract new vessels and therefore should be treated first. The laser treatment should respect potential conjugate PRL of fixation and the horizontal meridian, as much as possible. Microperimetry can be used to verify that a particular area on the retina has been destructed because it should result in a dense scotoma.

Minimal applications are hardly visible. The applications however can be permanently marked on any retinal image using overlays. These overlays of the location of the aiming beam of the therapeutic laser are indeed possible because of the use of gen-locked detectors in combination with appropriate barrier filters and image processing. These detector are the IR and visible wavelength detector as previously explained. Human reaction time is longer than 250 ms. Digital image processing can see faster any misalignment from an intended laser application location or a rapid increase in temperature. Digital image processing can effectively reduce the reaction time to one videoframe.

Although the description above contains many specificities, these should not be construed as limiting the scope of the invention but as merely providing illustrations of some of the presently preferred embodiments of this invention. Other embodiments of the invention including additions, subtractions, deletions, or modifications of the disclosed embodiment will be obvious to those skilled in the art and are within the scope of the following claims. The scope of the invention should be determined by the appended claims and their legal equivalents, rather than by the examples given.

I claim:

1. A combination of a scanning laser ophthalmoscope and external therapeutic laser source, for delivering a therapeutic laser beam of said laser source to the retina of an eye comprising the elements of:

A. said scanning laser ophthalmoscope, having at least one laser beam of a first wavelength that is scanned through a pivot point, and first detector means for obtaining a video image of said retina with said first detector of said scanning laser ophthalmoscope;

B. said external therapeutic laser source comprising an aiming beam of second wavelength and said therapeutic laser beam, further including a means to focus said therapeutic laser beam and said aiming beam, and supporting electronics controlling the size, duration and intensity of said therapeutic laser beam on the retina;

C. means for optically coupling said scanning laser ophthalmoscope with said therapeutic laser source including a beam splitter on which a coating is applied to permit said at least one laser beam and said aiming beam to be combined before entering said eye;

D. second detecting means in said scanning laser ophthalmoscope comprising second detector and optical means for detecting by preference said second wavelength, said second detecting means generating a video image that is synchronized with a video image produced by said first detector of said scanning laser ophthalmoscope;

E. digital image processing means comprising of a computer with a frame grabber card capable of generating overlay graphics, said frame grabber card further including means for synchronizing the video images produced by said first and said second detector to timing signals provided by said scanning laser ophthalmoscope, and output means capable of documenting the location of said aiming beam on the retina;

F. opto-mechanical means for coupling said scanning laser ophthalmoscope with said therapeutic laser source including a succession of mirror interfaces and structural support means joined together to move said aiming beam in such manner that a pivot point is created for said therapeutic beam, coincident with said pivot point of said scanning laser ophthalmoscope;

whereby optimal conditions of visualization are created to continuously observe the retina on a monitor and freely position said aiming beam on the retina, activate said therapeutic laser beam for a variable amount of time while observing and registering with said computer the position of said aiming beam on the retina.

2. A combination of a scanning laser ophthalmoscope and external therapeutic laser source, for delivering a therapeutic laser beam of said laser source to the retina of an eye according to claim 1, further comprising interrupting means including electronic circuitry to attenuate said therapeutic laser beam, said interrupting means allowing the attenuation of said therapeutic laser beam faster than human reaction time would allow in case of misalignment of said aiming beam on the retina as registered with said digital image processing means.

3. A combination of a scanning laser ophthalmoscope and external therapeutic laser source, for delivering a therapeutic laser beam of said laser source to the retina of an eye according to claim 1, further comprising modulating means for a laser source of visible wavelength in said scanning laser ophthalmoscope to create graphical stimuli in the visible laser raster of said scanning laser ophthalmosocpe, whereby a fixation target is provided for the observer facilitating the delivery of said aiming beam to the retina.

* * * * *